(12) United States Patent
Lombardi et al.

(10) Patent No.: US 8,043,364 B2
(45) Date of Patent: Oct. 25, 2011

(54) IMPLANT WITH ATTACHED ELEMENT AND METHOD OF MAKING SUCH AN IMPLANT

(75) Inventors: Sylvie Lombardi, Karlsruhe (DE); Wolfgang Supper, Karlsruhe (DE); Arne Briest, Karlsruhe (DE); Walter Garner, Bruchsal (DE)

(73) Assignee: Angiomed GmbH & Co. Medizintechnik KG, Karlsruhe (DE)

( * ) Notice: Subject to any disclaimer, the term of this patent is extended or adjusted under 35 U.S.C. 154(b) by 209 days.

(21) Appl. No.: 10/362,040

(22) PCT Filed: Aug. 16, 2001

(86) PCT No.: PCT/EP01/09467
§ 371 (c)(1),
(2), (4) Date: Jun. 27, 2003

(87) PCT Pub. No.: WO02/15820
PCT Pub. Date: Feb. 28, 2002

(65) Prior Publication Data
US 2004/0015228 A1 Jan. 22, 2004

(30) Foreign Application Priority Data
Aug. 18, 2000 (GB) .................................. 0020491.7

(51) Int. Cl.
*A61F 2/82* (2006.01)
(52) U.S. Cl. ..................... 623/1.34; 623/1.11; 623/1.16; 623/1.36
(58) Field of Classification Search ................. 623/1.11, 623/1.15, 1.18, 1.2, 1.35, 1.34, 1.36, 1.16
See application file for complete search history.

(56) References Cited

U.S. PATENT DOCUMENTS

| 5,741,327 | A | * | 4/1998 | Frantzen | 623/1.34 |
| 5,759,192 | A | * | 6/1998 | Saunders | 606/194 |
| 5,861,027 | A | * | 1/1999 | Trapp | 623/1.15 |
| 5,868,783 | A | * | 2/1999 | Tower | 606/198 |
| 6,022,374 | A | * | 2/2000 | Imran | 623/1.34 |

(Continued)

FOREIGN PATENT DOCUMENTS
DE 29621207 U1 1/1997
(Continued)

OTHER PUBLICATIONS

Database WIKIPEDIA, Sep. 11, 2007, "Lumen (anatomy)" XP 002453737 abstract.

(Continued)

*Primary Examiner* — Thomas J Sweet
*Assistant Examiner* — Christopher D Prone
(74) *Attorney, Agent, or Firm* — Rutan & Tucker, LLP

(57) ABSTRACT

A tubular implant having an axial end to which is attached a ring of spoons of a material different from that of the implant. In another aspect, the invention provides a method of attaching elements to an axial end of a tubular implant comprising the steps of providing said elements on one end of a support tube having a radius substantially that of the implant in its unexpanded configuration, abutting the implant and elements end-to-end, fixing the elements to the implant; and parting the elements from the support tube. In a third aspect, the invention provides an implant carrying an element of another material, the element and implant having complementary tapered mating surfaces for achieving a taper form fit of the element onto the implant.

26 Claims, 3 Drawing Sheets

U.S. PATENT DOCUMENTS

| | | | |
|---|---|---|---|
| 6,056,187 | A | 5/2000 | Acciai et al. |
| 6,293,966 | B1 | 9/2001 | Frantzen |
| 6,379,381 | B1 * | 4/2002 | Hossainy et al. ............ 623/1.42 |
| 6,540,777 | B2 * | 4/2003 | Stenzel ........................ 623/1.16 |
| 7,462,190 | B2 | 12/2008 | Lombardi |
| 2002/0193869 | A1 | 12/2002 | Dang |
| 2003/0144725 | A1 | 7/2003 | Lombardi |
| 2004/0015229 | A1 | 1/2004 | Fulkerson et al. |
| 2004/0073291 | A1 | 4/2004 | Brown et al. |
| 2004/0236409 | A1 | 11/2004 | Pelton et al. |
| 2004/0254637 | A1 | 12/2004 | Yang et al. |
| 2005/0049682 | A1 | 3/2005 | Leanna et al. |
| 2005/0060025 | A1 | 3/2005 | Mackiewicz et al. |
| 2005/0172471 | A1 | 8/2005 | Vietmeier |
| 2006/0216431 | A1 | 9/2006 | Kerrigan |
| 2007/0219624 | A1 | 9/2007 | Brown et al. |
| 2009/0200360 | A1 | 8/2009 | Wack |
| 2010/0070021 | A1 | 3/2010 | Wack et al. |
| 2010/0114298 | A1 | 5/2010 | Dorn et al. |

FOREIGN PATENT DOCUMENTS

| | | | |
|---|---|---|---|
| DE | 197 28 337 | A1 | 1/1999 |
| DE | 19728337 | A1 * | 1/1999 |
| DE | 4130431 | A1 | 3/1999 |
| DE | 29904817 | U1 | 5/1999 |
| DE | 10201151 | A1 | 7/2003 |
| EP | 0709068 | A2 | 5/1996 |
| EP | 0 709 068 | A3 | 6/1997 |
| EP | 0800800 | | 10/1997 |
| EP | 0847733 | A1 | 6/1998 |
| EP | 1157673 | | 11/2001 |
| EP | 1212991 | A2 | 6/2002 |
| EP | 1255507 | A1 | 11/2002 |
| EP | 1356789 | A1 | 10/2003 |
| EP | 1488763 | A2 | 12/2004 |
| FR | 2626046 | A1 | 7/1989 |
| WO | WO 95/03010 | * | 2/1995 |
| WO | 9733534 | A1 | 9/1997 |
| WO | WO9915108 | * | 4/1999 |
| WO | 0064375 | A1 | 11/2000 |
| WO | 0158384 | A1 | 8/2001 |
| WO | 03101343 | A1 | 12/2003 |
| WO | 2004058384 | A1 | 7/2004 |
| WO | 2005072652 | A1 | 8/2005 |
| WO | 2008006830 | A1 | 1/2008 |
| WO | 2008022950 | A1 | 2/2008 |
| WO | 2008068279 | A1 | 6/2008 |
| WO | 2008101987 | A1 | 8/2008 |

OTHER PUBLICATIONS

International Application No. PCT/EP2001/009467 International Preliminary Examination Report Sep. 17, 2002.

International Application No. PCT/EP2001/009467 International Search Report dated Feb. 18, 2002.

International Application No. PCT/EP2007/057041 filed Jul. 10, 2007 International Preliminary Report on Patentability dated Jan. 13, 2009.

International Application No. PCT/EP2007/057041 filed Jul. 10, 2007 International Search Report dated Oct. 18, 2007.

International Application No. PCT/EP2007/057041 filed Jul. 10, 2007 Written Opinion Jan. 10, 2009.

International Application No. PCT/EP2007/058416 filed Aug. 14, 2007 International Preliminary Report on Patentability dated Feb. 24, 2009.

International Application No. PCT/EP2007/058416 filed Aug. 14, 2007 International Search Report dated Nov. 22, 2007.

International Application No. PCT/EP2007/058416 filed Aug. 14, 2007 Written Opinion dated Feb. 23, 2009.

International Application No. PCT/EP2007/063347 filed Dec. 5, 2007 International Search Report dated Jun. 10, 2009.

International Application No. PCT/EP2007/063347 filed Dec. 5, 2007 Written Opinion dated Jun. 10, 2009.

International Application No. PCT/EP2007/063347 filed on Dec. 5, 2007 International Search Report dated Feb. 4, 2008.

International Application No. PCT/EP2008/052121 filed Feb. 21, 2008 International Preliminary Report on Patentability dated Aug. 26, 2009.

International Application No. PCT/EP2008/052121 filed Feb. 21, 2008 International Search Report dated May 19, 2008.

International Application No. PCT/EP2008/052121 filed Feb. 21, 2008 Written Opinion dated May 9, 2008.

U.S. Appl. No. 12/438,330, filed Feb. 20, 2009 Office Action dated Mar. 16, 2010.

U.S. Appl. No. 12/438,330, filed Feb. 20, 2009 Office Action dated Aug. 5, 2010.

U.S. Appl. No. 12/438,330, filed Feb. 20, 2009 Advisory Action dated Oct. 14, 2010.

EP 07802603.6 filed Aug. 14, 2007 Office Action dated Dec. 13, 2010.

U.S. Appl. No. 12/373,116 filed Jul. 14, 2009 Final Office Action dated Apr. 27, 2011.

U.S. Appl. No. 12/373,116 filed Jul. 14, 2009 Non-Final Office Action dated Nov. 10, 2010.

U.S. Appl. No. 12/438,330 filed Feb. 20, 2009 Office Action dated Mar. 4, 2011.

U.S. Appl. No. 12/517,096 filed Jun. 1, 2009 Office Action dated May 6, 2011.

* cited by examiner

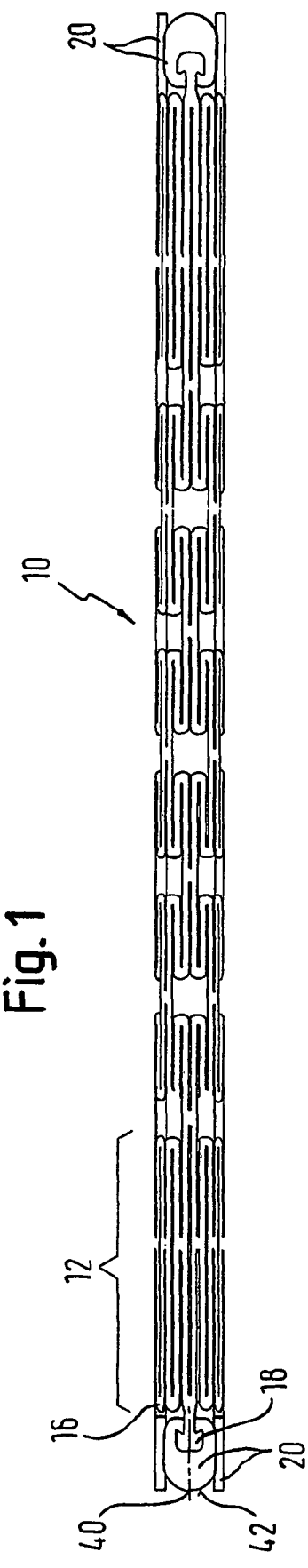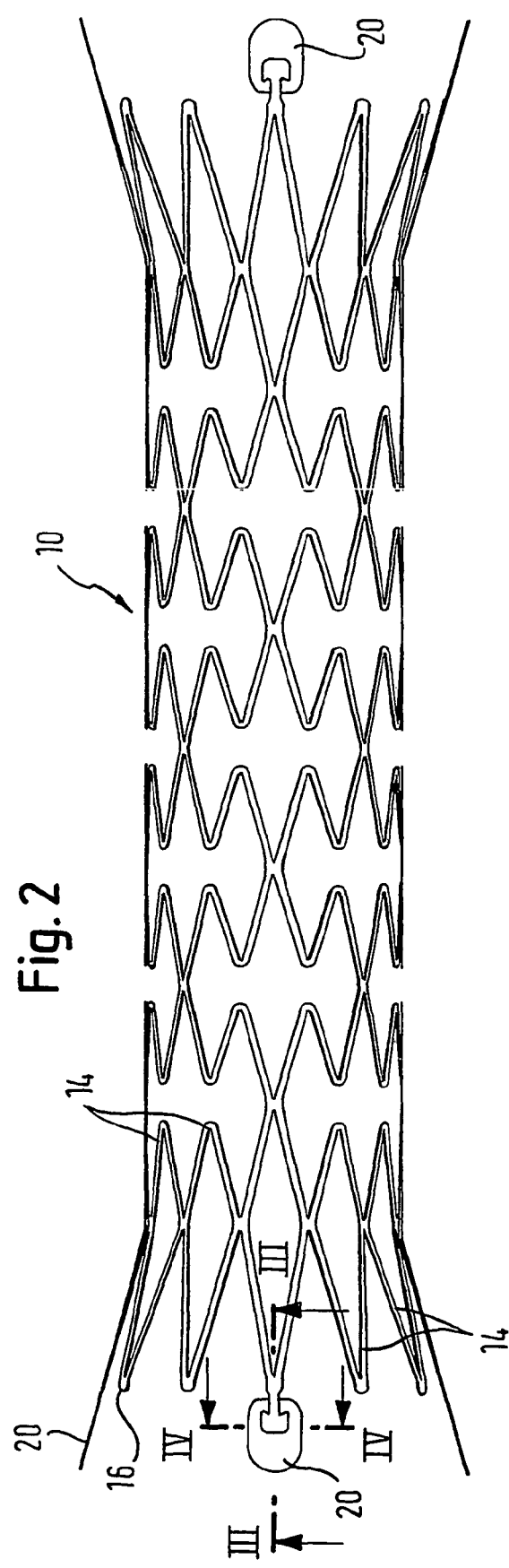

IMPLANT WITH ATTACHED ELEMENT AND METHOD OF MAKING SUCH AN IMPLANT

FIELD OF THE INVENTION

This invention relates to an implant, such as a stent formed from a stent material, to which is attached at least one element, such as a marker, made from a different material, such as a material having a radiopacity greater than that of the implant material. The invention also relates to a method of making such an implant.

Although the present invention has particular usefulness for attaching radiopaque markers to stents, it also has application to implants (filters, for example) other than stents, and to elements other than markers. Such elements could function as, for example, drug delivery vehicles, trauma inhibitors, or connectors to link the implant to another implant or to an implant extraction tool.

BACKGROUND ART

WO-A-95/03010 discloses a stent in the form of a metal tube having a long axis, a luminal surface and an abluminal surface, and a tube wall thickness, the tube carrying within the wall thickness a radiopaque marker made of a metal more radiopaque than the metal which forms the tube.

The stent of WO 95/03010 is created from a flat sheet of stainless steel material, by photochemical etching away of selected areas of the metal sheet, to leave behind an open lattice-work pattern, which is then rolled up into a tubular shape. A small round opening is provided at each end of the lattice area. Into each of these openings (called "eyelets") can be pressed a radiopaque marker of material such as gold, platinum, tungsten or iridium. The markers are positioned in the eyelets by crimping.

EP-A-800 800 also addresses the problem of poor radiopacity of stents, but advocates a different solution. In a nickel titanium shape memory alloy stent, it is proposed to provide, at one end at least of the cylinder which defines the stent, at least one detection element which has the shape of a tongue extending substantially in the longitudinal direction of the stent, this detection element having a width, in the circumferential direction of the stent cylinder, which is greater than the characteristic width, in the circumferential direction of the stent, of each of the struts which make up the lattice work pattern of the stent. It is the greater circumferential width of the tongue which renders it more radiopaque than the thinner struts of the lattice of the stent.

EP-A-847733 Biotronik discloses a stent which is an apertured cylinder of titanium, to each end of which is welded a meander-form ring of tantalum. The radiopacity of tantalum being much greater than that of titanium, this construction allows the locations of the ends of the stent cylinder to be determined radioscopically.

WO-A-00/64375 ACS was published Nov. 2, 2000, that is, after the present priority date. It discloses a stent made from wire or tube but with end rings of a material more radiopaque that its lengthwise centre section. Materials suggested for the centre section comprise Ni—Ti shape memory alloy (Nitinol) and stainless steel. Materials suggested for the end rings comprise tantalum, platinum, gold and platinum-iridium. To attach the end rings to the centre section, it is suggested to use, inter alia, laser welding.

EP-A-709 068 Medinol discloses providing stent ends with "protrusions having enough metal therein to make them X-ray visible". Gold and tantalum are mentioned as materials which are more visible under X-ray illumination than the stainless steel metal of the stent.

The disclosure of U.S. Pat. No. 6,022,374 is similar to that of WO-A-95/03010 mentioned above, in that it discloses an insert of radiopaque material within an eyelet formed in the stent. Mentioned as radiopaque materials are gold, platinum and alloys thereof.

DE-U-29904817 discloses a stent with axially extending projections at one end, at least. These projections can exhibit a thickening at their outer cantilevered ends. This concept can be compared with the disclosure of EP-A-800800, mentioned above.

U.S. Pat. No. 5,741,327 Frantzen discloses a stent with radiopaque markers attached to the ends of the body of the stent. In one embodiment, a circumferentially continuous serpentine marker element is attached to each end of the stent. This marker element can be of gold, silver, platinum or an alloy thereof. It is disclosed that the body of the stent can be from a nickel-titanium alloy. The circumferential marker is radially expansible along with the body of the stent. A circumferential marker is attached to an end of the stent body using one of a number of techniques including brazing, mechanical fastening, weaving or epoxy adhesive. One specific system of attachment disclosed involves the use of "receivers" that extend from the ends of the stent body. These receivers are configured to receive "tabs" provided on the marker ring. Each tab has a neck and a knob at the end of the neck and the knob is received into a co-operating rounded space of the receiver of the stent body. A laser is used to achieve local melting so that the receiver and tab are fused together.

The disclosures of WO 97/33534 is similar to that of WO 95/03010, in that it includes radiopaque rivets set in a stent of less radiopaque material.

SUMMARY

It is one object of the present invention to provide an implant, such as a stent, with an element of different material, securely fixed to the implant as such.

It is a more particular object of the present invention to provide a nickel-titanium shape memory alloy stent with a radiopaque marker which is compatible with the alloy of the stent; and biologically acceptable, and which is more effective and reliable than previous proposals.

According to one aspect of the present invention there is provided an implant as defined in claim 1 below. In a second aspect, there is provided an implant as claimed in claim 17 and, in a third aspect a method of attaching elements to an implant is provided, as claimed in claim 16.

With a ring of elements in the form of spoons, attached at one end of a tubular implant such as a stent, a more or less complete ring of attached material is presented in the radially compact delivery disposition of the stent, yielding potentially enhanced radiopacity. Even in the expanded disposition of the stent, a relatively small number of wide area spoons, say four, delivers relatively good radiopacity. However, the radiopacity in the compact disposition is particularly high, so that the present invention opens up the possibility to eliminate the previously indispensable radiopaque marker ring on the stent delivery system which reveals the location of an end of the stent. This in turn opens up the way to make delivery systems which are simpler in construction than the systems used up to now.

If interfitting shapes of the stent ends and attached elements are cut by a laser with its line of action always radial to the stent cylinder, then a tapered or beveled form fit between the stent and each attached element is achieved, enhancing the security of attachment and the precision of placement of each element attached to the stent.

This tapered form fit is particularly helpful when it is such that disengagement of the form-fit occurs by a radially-outward movement of the element relative to the stent cylinder. This is because, when the stent expands into its installed configuration, there is radially-inward pressure on the attached element from the surrounding bodily tissue, which resists its disengagement from the stent. This resistance complements and reinforces whatever other system is employed to fix the element to the stent.

Systems to fix an element to an implant can include welding, brazing, soldering, glueing, friction welding or variations of mechanical interlocks and press-fit configurations.

When creating stent lattices from sheet material, tubular sheet starting material is often considered advantageous. However, flat sheet material also is advantageous in some systems, such as those in which the stent element is rolled up like a carpet. When laser-cutting the lattice, the above-mentioned tapered form fit can be readily engineered when cutting the sheet in planar form.

In a particularly advantageous embodiment, a stent is formed from sheet material in the form of a tube, and is provided at each end with a plurality of marker carrier portions, to each of which is mounted a radiopaque marker of radiopaque material, in the form of a spoon. Each of the carriers has a luminal surface, an abluminal surface, and a peripheral surface through the thickness of the stent tube. It is this peripheral surface which provides one of two complementary mating surfaces for making the stent/marker attachment. The complementary marker itself has two major surfaces, one of which is luminal and the other is abluminal, and a peripheral surface around the major surfaces. However, within the area of the major surfaces is a cavity portion. The periphery of this cavity defines a female element for engagement with a male portion of the stent tube marker carrier portion, the male and female peripheral surfaces providing complementary tapering form-fit surfaces.

Preferably each such ring of markers has four marker spoons in it. Increasing beyond four reduces the size of each marker. In the expanded configuration of the stent, visibility of the stent increases with the physical area of each separate marker, so large markers are preferred because they make the expanded stent more visible.

It is preferred that the markers together make a more or less continuous ring around the stent in its small diameter configuration prior to its deployment by expansion.

According to the second aspect of the present invention there is provided a method for making from sheet material a tubular implant, such as a stent, which expands, during its deployment, from a smaller radius delivery disposition to a larger radius deployed disposition, the method comprising the steps of:

1. providing at least one terminal element on one end of a support of sheet material arranged as a cylinder with its radius being that of the said delivery disposition;
2. presenting the tubular implant in its smaller radius, end-to-end with the support, such that the terminal element abuts the implant;
3. fixing the terminal element to the implant; and
4. parting the terminal element from the support.

One of the problems involved in fixing radiopaque markers to stents is the difficulty of aligning the markers with the stent in order to fix the markers to the stent in exactly the right orientation and position relative to the stent as such. This second aspect of the invention ameliorates this problem by presenting markers as terminal elements on one end of a cylindrical support of sheet material which has the same radius as the stent in its unexpanded disposition. This is because it is relatively easy to arrange in co-linear fashion the cylinder of the stent and the cylinder of the support and, with both of these items having the same radius, the cylindrical end surface of the support would be in abutment with the cylindrical end surface of the stent. Now, if the cylindrical end surface of the support exhibits a plurality of terminal elements which are destined to become elements attached to the stent, the process of fixing these markers to the stent can be effected by welding the elements to the end of the stent, while they are in end-to-end abutment with the stent end. Then, when this welding step has been completed, it should be a simple further step to part the marker elements from the support cylinder, for example, by laser-cutting through the thickness of the sheet material which forms the support.

It will be appreciated that the terminal elements will have the curvature of the support cylinder, which curvature will correspond to the curvature of the stent in its delivery disposition. Thus, when the stent expands to its deployed disposition, and the curvature of the terminal elements remains unchanged, these elements will have a radius of curvature somewhat smaller than the radius of the expanded stent cylinder. However, this discrepancy in curvature will not be significant because the terminal elements will be, to a greater or lesser extent, embedded in the bodily tissue forming the wall of the lumen in which the stent is deployed. Indeed, the elements might have no curvature at all. This would be the case if, for example, the main stent manufacturing steps are performed on flat sheet material, while it is planar, with the stent lattice then being rolled up for installation into a delivery system. The rolling up step would impart a curvature to the stent, but not necessarily to the attached elements.

The invention is particularly well adapted to the technical field of shape memory alloy stents, specifically those made of Nitinol, and the attachment to them of terminal marker elements of tantalum.

In order to make Nitinol stents more visible to radiation, by the provision of tantalum markers, one would wish to import a greater mass of tantalum, but without any increase in the wall thickness of the stent at the locations of the markers. The ideal stent has minimal wall thickness, not only for keeping the stented bodily lumen as open to fluid as possible, but also to keep the stent delivery system with as small a cross-sectional profile as possible. The present invention furthers this objective, in the following way.

The cylinder of sheet material which provides the terminal elements and support tube is amenable to laser-cutting of the terminal elements out of the material of the tube. Accordingly, virtually all of the material forming the circumference of the tube is available for contribution to the making of the terminal elements. The terminal elements can take up the entire circumference of the support tube, except for the thickness of the laser cuts between adjacent terminal elements around the circumference. Accordingly, for the stent in its small radius delivery disposition, there could be virtually an entire circumference of radiopaque tantalum marker material provided at each end of the stent, with the only breaks in the continuous ring around the circumference being the laser cuts between adjacent marker elements.

In one specific embodiment, there is laser-cut from the support tube a pattern of four terminal marker elements, each extending around one quarter of the circumference of the support tube. Each of these marker elements takes up virtually ninety degrees of the circumference of the stent in its delivery disposition.

The exact shape of the outline of each terminal element, and the exact shape of the abutment surface on it which contacts the corresponding abutment surface of the end of the implant, is a matter of design freedom and choice. At the moment, for implants which are stents, and attached elements which are radiopaque markers, it is contemplated to provide each element with more or less straight sides to face the adjacent marker elements around the circumference of the stent, but with an arcuate end surface and a female rebated internal abutment surface to receive a corresponding arrowhead shape male marker carrier portion on the end ring of the stent. Such a pattern of shape features is described in more detail below by reference to the accompanying drawings.

With a male/female interfit of the marker element and stent end ring carrier portions, with rebated surfaces, and with the respective peripheral mating surfaces extending along radial lines to the stent cylinder, a snap fit interengagement of the stent cylinder and support cylinder can be arranged, further helping to accomplish the objective of precise position and orientation of the marker elements relative to the stent cylinder.

In any event, a convenient way to fix permanently and reliably the tantalum marker elements to a Nitinol stent cylinder is by laser-welding. When laser-cutting the lattice of a stent from a cylinder of sheet material, the line of action of the laser is invariably on a radius of the tubular workpiece. If the co-operating surfaces of the stent, and of its spoons, end elements or markers, are both cut with a laser on a radial line of action, then there will tend to be a self-centering and self-aligning effect when the support tube is offered up, end-to-end to the stent in its small radius of compressed configuration. This effect enhances the value of the method of the present invention in building stent assemblies to precise tolerances and with its end elements securely attached.

For a better understanding of the present invention, and to show more clearly how the same may be carried into effect, reference will now be made, by way of example, to the accompanying drawings.

BRIEF DESCRIPTION OF THE DRAWINGS

FIG. 1 is a view from the side of a stent tube, looking along a line which intersects the long axis of the tube and is perpendicular to it the stent being in its smaller radius delivery configuration; and FIG. 2 is the view of FIG. 1, but with the stent in its deployed, relatively large radius disposition;

DETAILED DESCRIPTION

Figure 3:
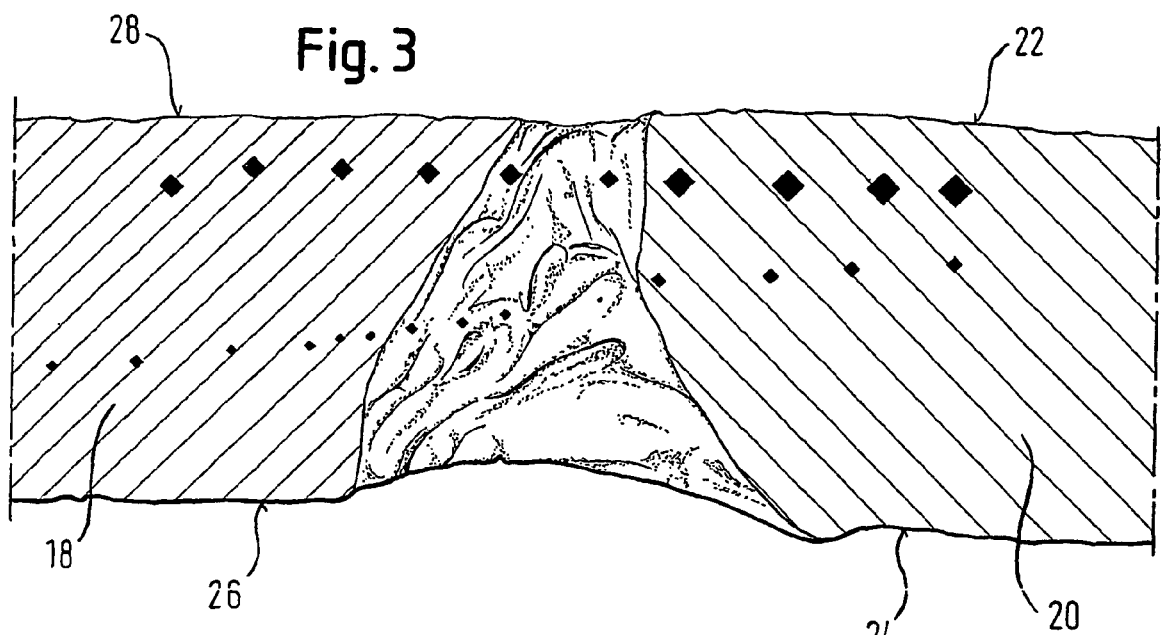
FIG. 3 is a micrograph taken on a section through the line III-III shown in FIG. 2.

Skilled readers will appreciate that the material of the stent tube and its markers lies all in a circular cross-section with a wall thickness as small as possible, so as to be consistent with the objective of maintaining a bodily lumen as open as possible. The stent cylinder can be formed from seamless tubular starting material, or from flat material rolled into a tube (which thus exhibits some sort of seam).

Skilled readers will also be well aware that there have been a very large number of proposals for strut patterns in the tubular configurations of stents. Whereas FIG. 1 shows an expandable strut pattern in a form which is particularly preferred for the present Applicant, nevertheless any other strut pattern will have points in it which define an end to the cylinder of the stent, and therefore will have points at the ends of the stent cylinder where markers can be attached.

Readers will also appreciate that self-expanding stents are delivered to stenting locations in a radially compressed form, so that the aggregate length, in the circumferential direction, of all of the markers in any particular ring around the axis of the stent tube cannot exceed the circumference of the stent tube in its compressed delivery configuration. In the embodiment shown in FIG. 1, each of the four markers has a circumferential length just less than the circumferential length of three cycles of the zigzag pattern which defines the end ring of the stent cylinder so that, when the stent cylinder is compressed, with all the struts of the zigzag ring laying close to each other, the adjacent radiopaque markers will also lie closely adjacent each other in the circumferential direction.

As can be seen in FIG. 1, the end ring 12 of the stent cylinder 10 is constituted by a succession of struts 14 which zigzag their way around the full circumference of the ring 12. There is a vertex 16 where each two successive struts intersect, with the end of the stent cylinder being defined by the succession of vertices 16. A marker carrier portion 18 is located at every third end vertex 16, and fitted to each carrier portion 18 is a marker element 20. In the illustrated embodiment, the stent is made from Nitinol, nickel-titanium shape memory alloy, and each marker element is of tantalum. In other embodiments, the stent could be of stainless steel. The attached elements could be of tantalum, platinum, gold or iridium, for example.

Figure 4:
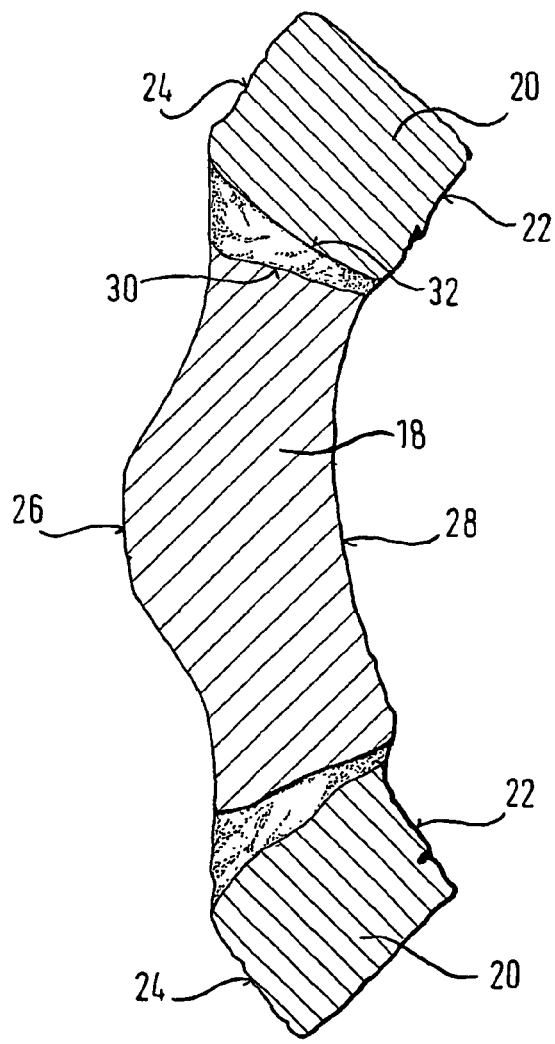
FIG. 4 is a micrograph taken on a section through the line IV-IV shown in FIG. 2.

Referring now to FIGS. 3 and 4 together, the tantalum marker 20 has a luminal surface 22 and an abluminal surface 24, with the abluminal surface 24 being in line with the abluminal surface 26 of the stent cylinder and the luminal surface 22 of the marker being in line with the luminal surface 28 of the stent cylinder. FIG. 4 shows that the peripheral surface 30 of the carrier portion 18 is tapered inwardly from the abluminal surface 26 to the luminal surface 28 of the stent cylinder. The marker 20 has a co-operating complementary tapered mating surface 32, therefore also defining part of a cone with its vertex lying radially inside the stent cylinder. It will be appreciated that achievement of the form fit-shown in FIG. 4 is by advancing the carrier portion 18 radially inwardly into the cavity defined by surface 32 of the marker 20 until there is a tight fit between the two complementary tapered surfaces 30 and 32, corresponding with a lining up of the luminal and abluminal surfaces of the stent cylinder and marker.

In FIG. 4 surfaces 24 and 26 face a bodily lumen wall. The stent cylinder 10 with its end ring 12 and its carrier portions 18 are serving to hold back the bodily lumen wall tissue from radially inward encroachment (rightwards in FIG. 4). The tissue presses radially inward also on the marker 20, tending to dislodge the form-fit. However, in laser-welding the tantalum spoon 20 to the Nitinol carrier portion 18, melting and flow of Nitinol around the tantalum spoon achieves re-entrant locking surfaces, as can be seen on the photomicrograph, which effectively resist such dislodging.

The present invention aims to assist the attachment of tantalum markers to Nitinol stents, for example by laser-welding, and make it even more reliable and secure. The melting point of tantalum is around 3000° C., and that of Nitinol around 1200° C., rendering it difficult to achieve a good bond purely by welding. However, the tapered close fit between the two metals, and the flow of Nitinol around the tantalum during welding, achieves a secure mechanical interlock between the stent and the marker 20.

It is conventional to form the lattice patterns of Nitinol stents by laser-cutting. The line of action of a laser for cutting the tapered mating surfaces 30 of the carrier portion 18 in the stent are achieved by aligning the laser in the normal radial direction of intersecting the long axis of the stent tube.

As to the number of markers in one circumference of the stent, optimum radiopacity is accomplished when the markers at each end of the stent make up a virtually unbroken solid ring of marker material around the full circumference. In the case shown there is a marker on every third end vertex of the stent, with 4 markers at each end of the stent, and 12 zigzag vertices around the circumference of the stent. This, however, is not to exclude the possibility of fewer markers at each end of the stent, including the extreme case, seen in wo 95/03010, mentioned at the beginning of this specification, that there is only one marker at each end of the stent cylinder.

Turning now to the second aspect of the invention, and to the assembly of the markers 20 onto the stent 10, one can see from FIG. 1 how the four markers 20 at each end of the stent cylinder form a virtually unbroken ring of material having a diameter exactly the same as that of the stent cylinder 10 in the delivery disposition of FIG. 1.

Figure 5:
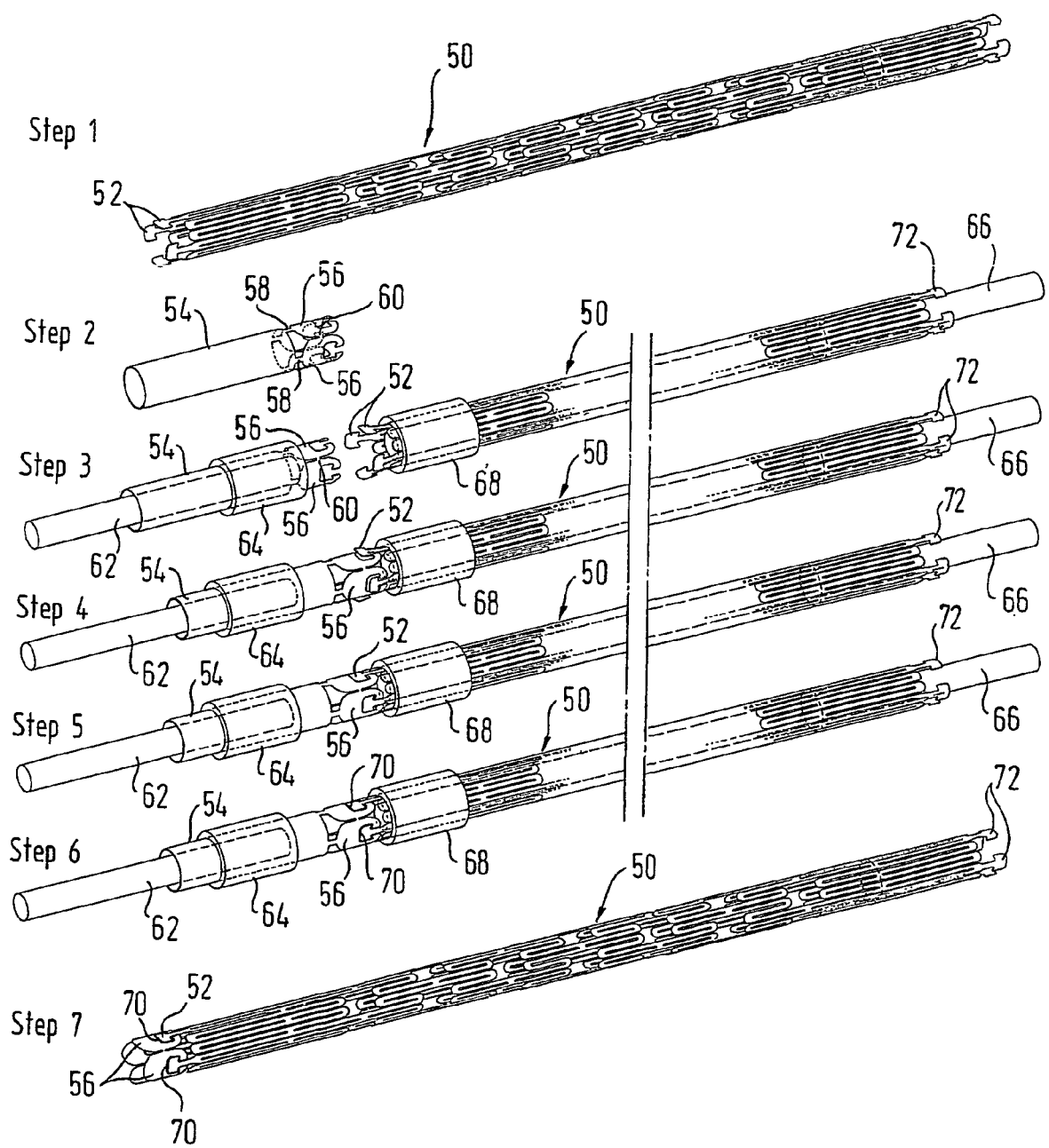
FIG. 5 shows schematically a stepwise manufacturing process.

FIG. 5 shows the four adjacent markers 56 are all cut from a single tube of tantalum material having the same radius as the stent cylinder 10, a laser having been used to cut around the periphery of each marker, including the rebated portion in the centre of the marker which receives the marker portion 18 of the stent. The only place where the thus cut marker element 56 remains attached to the carrier tube is at the central tip 40 (FIG. 1) of the arcuate surface 42 which defines the peripheral end surface of the marker 20 remote from the stent cylinder 10.

A support cylinder 54 which includes the four markers 20, 56 attached at their tips 40 is offered up to the stent cylinder 10, the two cylinders being co-linear and coaxial. There is then a snap fit of the marker portions 18 of the stent 10 into the receiving recess of each marker 20. Once the marker portions 18 are secure within the recesses of the respective markers 20, a laser can be deployed to produce a laser weld between the marker portion 18 and the marker 20. During welding; the Nitinol adjacent the tantalum marker melts locally and to a limited extent flows around the tantalum, thereby effectively form-locking the marker to the stent. With this laser welding accomplished, a laser can then be brought into play, to part at marker tip 40 each individual marker 20 from the carrier tube 54 which has supported it up to that point. With this parting away of the markers 20 from their carrier tube, the stent can then be separated from the carrier tube, with the markers 20 securely welded to the stent 10.

Readers will immediately appreciate from the above description, taken in conjunction with the drawings, that the markers 20 have the general form of a spoon. That is to say, the markers have two major dimensions and one minor dimension, namely, the thickness in the radial direction of the stent. The two major surfaces have a length direction in the length direction of the stent and are more or less flat in that direction. However, in the transverse direction, circumferential with respect to the stent cylinder, the markers are curved so that they exhibit a luminal surface which is concave and an abluminal surface which is convex. This curvature is also exhibited in the transverse direction of a cutlery spoon.

Further, each marker 20 has a near end surface in which is something akin to the shaft of a cutlery spoon, namely, the marker portion 18 of the stent. Opposite this end surface is another end surface, relatively remote from the stent, which is not attached to the stent and is arcuate on its periphery. This is reminiscent of the arcuate (in the sense of presenting an outwardly convex shape) peripheral end surface of a cutlery spoon, remote from the shaft of the spoon.

In FIG. 5 are shown seven steps, in FIGS. 5(1) to 5(7), of a process for manufacturing an implant in accordance with the invention, which is a stent of Nitinol having at each of its ends a ring of tantalum spoons.

Step 1 is to cut with a laser a tube of Nitinol material in order to produce a stent precursor 50 having at each ends a ring of four marker carrier portions 52 each having a shape which has some slight resemblance to an arrowhead shape. In the example shown here, the Nitinol tube has a wall thickness of 0.24 mm and a nominal diameter of 1.6 mm.

FIG. 5(2), showing step 2, shows a tube of tantalum 54 which has the same 1.6 mm nominal diameter and 0.24 mm wall thickness but a shorter length than the stent precursor 50. At one end of the tantalum tube 54 has been laser-cut a ring of four spoons 56. A narrow bridge of material 58 at the tip 40 on the arcuate end surface of each spoon connects each spoon 56 to the tube 54, and a similar narrow bridge 60 links each spoon 56 at its widest point to the corresponding point on the next adjacent spoon 56 on each side. In this way, the spoons are all linked up in a ring and each individually still part of the tantalum tube 54.

In FIG. 5(3), step 3 of the manufacturing process includes placing a core 62 inside the tantalum tube 54, and a surrounding sleeve 64 radially outside the tube 54. The core 62 and sleeve 64 do not extend as far as the ring of spoons 56 but terminate just short of that ring. Likewise, Nitinol tube 50 receives a core 66 and a surrounding sleeve 68 which again stop just short of the ring of carrier portions 52. In a jig, the two spaced cores 62 and 66 are linked through their outer ends so as to be maintained co-axial and co-linear, which therefore assures that the ring of carrier portions 52 and ring of spoons 56 are themselves co-axial and co-linear. FIG. 5(3) shows each of the carrier portions 52 tilted slightly radially outwardly, to indicate that this is feasible, for offering up the carrier portions 52 into the corresponding recesses of the corresponding spoons 56, as explained above, and as shown in FIG. 5(4).

In FIG. 5(4), it is shown how manual manipulation of the carrier portions 52 can be used to get them into the corresponding recesses of the spoons 56, when the cores 62 and 66 are brought closer to each other in the above-mentioned jig. This manual manipulation, of each individual carrier portion 52 in turn, is carried out manually, under a microscope.

FIG. 5(5) shows the carrier portions 52 duly fitted within the corresponding recesses of the spoons 56.

FIG. 5(6) differs from the preceding method step of FIG. 5(5) by the presence of a welding bead 70 which connects each one of the spoons 56 with its corresponding carrier portion 52, around the periphery of the arrowhead of the carrier portion 52. This welding bead is a result of a laser-welding step which occurs between illustrated steps 5 and 6 but is not shown as such in FIG. 5. In itself, it will be familiar to readers skilled in Nitinol stent manufacture.

FIG. 5(7) differs from FIG. 5(6) in that the cores 62 and 66 and the rings 64 and 68 have been removed, to leave a ring of spoons 56 duly welded to one end of the Nitinol tube stent precursor 50. With a laser, the bridges 58 and 60 are cut through, so as to release each spoon from the tantalum tube 54 and the spoons adjacent to it.

Clearly, if it desired to place a ring of spoons at the other end of the stent tube 50 then the process can be repeated at this other end. Indeed, in FIG. 5, a ring of carrier portions 72 is shown at the other end of the stent tube 50.

Once the spoons have been placed as desired on the precursor tube 50 of the stent, then this precursor tube can be subjected to the normal successor manufacturing steps, including the step of expanding the stent precursor to a desired larger diameter and then annealing it at that diameter in order to "set" a stent shape in the austenitic phase of the Nitinol material, which is the shape that it is desired the stent should revert to, in the body, upon deployment from a stent delivery system. Such a set shape might include a central cylindrical portion of the stent, and flared portions at each end, with the ring of carrier portions 52 and spoons 56 themselves forming part of the flared portion of the end of the stent. As tantalum has a melting point so much higher than that of Nitinol, there is no likelihood that the Nitinol annealing step will in any way adversely affect the spoons and welding beads at each end of the stent cylinder.

The scope of protection of the claims which follow is not to be limited to the embodiments described in detail above. Readers will appreciate that the detailed description is to assist in realising embodiments within the scope of the claim rather than to set a limit on the scope of protection.

The invention claimed is:

1. A method of attaching elements to an axial terminal end of a tubular implant comprising:
    providing said elements on one end of a support tube having a radius substantially that of the implant in its unexpanded configuration, adjacent of said elements unconnected,
    abutting the implant and elements end-to-end,
    fixing the elements to the implant, the elements and implant having tapered mating surfaces tapering in a radial direction of the implant, and
    parting the elements from the support tube.

2. A method as claimed in claim 1, wherein the elements comprise spoons.

3. An implant comprising:
    a wire or sheet material arranged in the form of a metal tube having a long axis, a luminal surface and an abluminal surface, and a radial wall thickness between said surfaces, the implant carrying within the wall thickness a plurality of separate elements made of an element material other than the wire or sheet material, the elements being disposed at a terminal end of the implant, and
    the elements and the tube having complementary tapered mating surfaces extending longitudinally from the terminal end along a longitudinal axis of the tube for achieving a taper form fit of the elements on to the tube along a plane traversing the radial wall thickness.

4. An implant as claimed in claim 3, wherein each of the elements comprises a spoon.

5. A medical device, comprising:
    an implant defining a longitudinal axis and a terminal implant end;
    a plurality of independent markers; and
    a plurality of marker carriers each having an arrowhead shape with a barbed arrowhead base end disposed to engage the terminal implant end and an opposing end directed away from the terminal implant end, wherein a periphery of the marker carrier is tapered inwardly toward the longitudinal axis.

6. The device of claim 5, the arrowhead shape including at least one barb pointing in a direction towards the terminal implant end.

7. The device of claim 6, the at least one barb defining a gap between the at least one barb and a marker carrier shaft joining the implant and the marker carrier.

8. A medical device, comprising:
    an implant defining a longitudinal axis and a terminal implant end;
    a plurality of separate markers; and
    a plurality of marker carriers disposed at the terminal implant end, each of the marker carriers including a tapered periphery, a first portion disposed to engage the terminal implant end, and a second portion, the first portion disposed between the terminal implant end and the second portion and defining a first direction from the first portion to the second portion, the first and second portions having widths transverse to the direction, the first portion width being less than the second portion width,
    the marker carriers including a transition portion defining a transition from the first portion width to the second portion width, the transition portion including at least one projection disposed to extend from the first portion in a second direction opposite to the first direction.

9. A medical device, comprising:
    an implant defining a longitudinal axis and a terminal implant end;
    a plurality of markers circumferentially separated; and
    a plurality of marker carriers disposed at the terminal implant end, each of the marker carriers including a tapered periphery, a first portion disposed to engage the terminal implant end, and a second portion, the first portion disposed between the terminal implant end and the second portion and defining a direction from the first portion to the second portion, the first and second portions having widths transverse to the direction, the first portion width being less than the second portion width,
    the marker carriers including a transition portion defining a transition surface from the first portion width to the second portion width, the transition surface having an undulation along a plane orthogonal to the direction.

10. A medical device, comprising:
    an implant defining a longitudinal axis and a terminal implant end;
    a plurality of markers circumferentially separated; and
    a plurality of marker carrier disposed at the terminal implant end, each of the marker carriers including a tapered periphery, a first portion disposed to engage the terminal implant end, and a second portion, the first portion disposed between the terminal implant end and the second portion and defining a direction from the first portion to the second portion, the first and second portions having widths transverse to the direction, the first portion width being less than the second portion width,
    the marker carrier including a transition portion defining a transition surface from the first portion width to the second portion width, the transition surface defining a gap between the first portion and the second portion along a plane orthogonal to the direction.

11. A medical device, comprising:
    an implant defining a longitudinal axis and a terminal implant end;
    a plurality of marker carriers disposed at the terminal implant end, each of the marker carriers having a wide portion and a narrow portion, the narrow portion disposed between the wide portion and the implant end, the wide portion defining an exterior surface disposed in a plane traversing the longitudinal axis; and
    a plurality of separate markers, each disposed to engage the exterior surface of the wide portion in order to resist radially-inward movement relative to its respective marker carrier.

12. The device of claim 11, each marker disposed to engage the entire exterior surface of the wide portion within the plane traversing the longitudinal axis.

13. The device of claim 11, the narrow portion defining an exterior surface disposed in a plane orthogonal to the longitudinal axis, each marker disposed to engage the exterior surface of the narrow portion.

14. A medical device, comprising:
an implant defining a longitudinal axis and a terminal implant end;
a plurality of marker carriers disposed at the terminal implant end, each of the marker carriers having a wide portion and a narrow portion, the narrow portion disposed between the wide portion and the terminal implant end; and
a plurality of separate markers, each having an exterior surface defining a cavity, at least a portion of a respective one of the marker carriers disposed within the cavity such that the marker carriers resist radially-inward movement of the markers.

15. The device of claim 14, the wide portion disposed entirely within the cavity.

16. The device of claim 14, a part of the narrow portion disposed within the cavity.

17. A medical device comprising:
an implant defining a longitudinal axis and a terminal implant end;
a plurality of marker carriers disposed at the terminal implant end, each having an outer peripheral surface disposed in a plane at least in part intersecting the longitudinal axis; and
a plurality of separate markers, each having an inner peripheral surface disposed in a plane at least in part intersecting the longitudinal axis,
at least a portion of the outer peripheral surface abutting at least a portion of the inner peripheral surface along a rebated surface to engage each of the markers with its respective marker carrier, the inner and outer surfaces abutting when an outer circumferential surface of each of the marker carriers aligns with an outer circumferential surface of its respective marker.

18. A medical device comprising:
an implant defining a longitudinal axis and a terminal implant end;
a plurality of marker carriers disposed at the terminal implant end, each having an outer peripheral surface disposed in a plane at least in part intersecting the longitudinal axis; and
a plurality of separate markers, each having an inner peripheral surface disposed in a plane at least in part intersecting the longitudinal axis,
at least a portion of the outer peripheral surface abutting at least a portion of the inner peripheral surface along a rebated surface to engage each of the markers with its respective marker carrier, the inner and outer surfaces abutting when an inner circumferential surface of each of the marker carriers aligns with an inner circumferential surface of its respective marker.

19. A medical device comprising:
an implant defining a longitudinal axis and a terminal implant end;
a plurality of marker carriers disposed at the terminal implant end, each having an outer peripheral surface disposed in a plane at least in part intersecting the longitudinal axis; and
a plurality of unconnected markers, each having an inner peripheral surface disposed in a plane at least in part intersecting the longitudinal axis,
at least a portion of the outer peripheral surface abutting at least a portion of the inner peripheral surface along a rebated surface to engage each of the markers with its respective marker carrier, the inner or outer peripheral surfaces defining a tapered edge in a plane traversing the longitudinal axis.

20. A medical device comprising:
an implant defining a longitudinal axis and a terminal implant end;
a plurality of marker carriers disposed at the terminal implant end, each having an outer peripheral surface disposed in a plane at least in part intersecting the longitudinal axis; and
a plurality of unconnected markers, each having an inner peripheral surface disposed in a plane at least in part intersecting the longitudinal axis;
at least a portion of the outer peripheral surface abutting at least a portion of the inner peripheral surface along a rebated surface to engage each of the markers with its respective marker carrier, at least a portion of the outer peripheral surface abutting at least a portion of the inner peripheral surface.

21. A medical device comprising:
an implant defining a longitudinal axis and a terminal implant end;
a plurality of marker carriers disposed at the terminal implant end and having an outer peripheral surface disposed in a plane at least in part intersecting the longitudinal axis; and
a plurality of disconnected markers, each having an inner peripheral surface disposed in a plane at least in part intersecting the longitudinal axis,
at least a portion of the outer peripheral surface abutting at least a portion of the inner peripheral surface along a rebated surface to engage each of the markers with its respective marker carrier, each marker carrier including a welding area portion defining the outer peripheral surface, the welding area portion consisting of a melted portion of the marker carrier.

22. A method, comprising:
inserting a marker carrier disposed on a terminal end of an implant into an internal cavity of one of a plurality of unconnected markers, the cavity defined by a peripheral surface of the one marker;
abutting the marker peripheral surface against an exterior surface of the marker carrier, the abutting surfaces having a complimentary taper in a direction traversing a thickness of the marker; and
joining the marker to the marker carrier.

23. A method, comprising:
aligning a plurality of unconnected markers extending from a tube with a plurality of respective marker carriers extending from a terminal end of a tubular implant;
inserting the marker carriers into internal cavities of the markers, the cavities defined by a peripheral surface of the marker;
joining each of the markers to the marker carriers at complimentary tapered mating surfaces tapering in a radial direction of marker carrier; and
separating the tube from the markers.

24. A method, comprising:
disposing a plurality of unconnected markers in a predetermined position relative to a plurality of respective marker carriers engaging a terminal end of a tubular implant defining a longitudinal axis;

maintaining the predetermined position in a longitudinal direction parallel to the axis and in a circumferential direction about the axis with opposing mating surfaces of the markers and marker carriers; and maintaining the predetermined position in a radial direction relative to the axis with opposing angled mating surfaces.

25. A method, comprising:

disposing a plurality of separated markers in a predetermined position relative to a longitudinal axis defined by a tubular implant disposed with a terminal implant end proximate the markers;

disposing a plurality of marker carriers extending from the terminal implant end to abut peripheral edges of the markers; and aligning the marker carriers relative to the markers by engaging mating surfaces having a cross-sectional taper in a plane traversing the axis.

26. A method, comprising:

disposing a plurality of separated markers proximate a terminal end of a tubular implant defining a longitudinal axis;

deflecting a plurality of marker carriers extending from the terminal end of the tubular implant away from the axis to a radial distance greater than a radial distance between the markers and axis;

moving the marker carriers to a position radially adjacent the markers;

deflecting the marker carriers toward the axis to a radial distance equal to the radial distance between the markers and axis; and engaging the markers with the marker carriers at complimentary tapered mating surfaces tapering in a radial direction of the implant.

* * * * *